United States Patent
Struve

(10) Patent No.: US 9,750,944 B2
(45) Date of Patent: *Sep. 5, 2017

(54) MRI-CONDITIONALLY SAFE MEDICAL DEVICE LEAD

(75) Inventor: Roger Struve, St. Paul, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 1580 days.

This patent is subject to a terminal disclaimer.

(21) Appl. No.: 12/938,113

(22) Filed: Nov. 2, 2010

(65) Prior Publication Data

US 2011/0160818 A1    Jun. 30, 2011

Related U.S. Application Data

(60) Provisional application No. 61/291,076, filed on Dec. 30, 2009.

(51) Int. Cl.
  *A61N 1/37* (2006.01)
  *A61N 1/08* (2006.01)

(52) U.S. Cl.
  CPC ...... *A61N 1/3718* (2013.01); *A61N 2001/086* (2013.01)

(58) Field of Classification Search
  CPC .................................................. A61N 1/3718
  USPC ........................................................ 607/116
  See application file for complete search history.

(56) References Cited

U.S. PATENT DOCUMENTS

| | | |
|---|---|---|
| 3,614,692 A | 10/1971 | Rozelle et al. |
| 4,131,759 A | 12/1978 | Felkel |
| 4,135,518 A | 1/1979 | Dutcher |
| 4,146,036 A | 3/1979 | Dutcher et al. |
| 4,209,019 A | 6/1980 | Dutcher et al. |
| 4,253,462 A | 3/1981 | Dutcher et al. |

(Continued)

FOREIGN PATENT DOCUMENTS

| | | |
|---|---|---|
| CA | 1154833 A1 | 10/1983 |
| CN | 1762510 A | 4/2006 |

(Continued)

OTHER PUBLICATIONS

International Search Report and Written Opinion issued in PCT/US2010/055653, mailed Feb. 1, 2011, 14 pages.

(Continued)

*Primary Examiner* — Eric D. Bertram
(74) *Attorney, Agent, or Firm* — Faegre Baker Daniels LLP

(57) ABSTRACT

An implantable medical device lead includes an inner conductor assembly coupled to a first electrode at a distal end of the inner conductor assembly and an outer conductive coil extending coaxially with the inner conductor assembly and coupled to a second electrode. The inner conductor assembly includes one or more filars arranged in a plurality of serially connected current suppression modules. Each current suppression module includes a first coil of the one or more filars wound in a first winding direction, a second coil of the one or more filars coaxial with the first winding and wound in a second winding direction opposite the first winding direction, and a third coil of the one or more filars coaxial with the first and second windings and wound in the first winding direction. The outer conductive coil includes one or more filars wound in the first winding direction.

12 Claims, 4 Drawing Sheets

(56) References Cited

U.S. PATENT DOCUMENTS

| | | |
|---|---|---|
| 4,350,169 A | 9/1982 | Dutcher et al. |
| 4,381,013 A | 4/1983 | Dutcher |
| 4,404,125 A | 9/1983 | Abolins et al. |
| 4,437,474 A | 3/1984 | Peers-Trevarton |
| 4,484,586 A | 11/1984 | McMickle et al. |
| 4,493,329 A | 1/1985 | Crawford et al. |
| 4,574,800 A | 3/1986 | Peers-Trevarton |
| 4,643,202 A | 2/1987 | Roche |
| 4,643,203 A | 2/1987 | Labbe |
| 4,649,938 A | 3/1987 | McArthur |
| 4,869,970 A | 9/1989 | Gulla et al. |
| 5,002,067 A | 3/1991 | Berthelsen et al. |
| 5,003,975 A | 4/1991 | Hafelfinger et al. |
| 5,020,545 A | 6/1991 | Soukup |
| 5,056,516 A | 10/1991 | Spehr |
| 5,074,313 A | 12/1991 | Dahl et al. |
| 5,144,960 A | 9/1992 | Mehra et al. |
| 5,201,865 A | 4/1993 | Kuehn |
| 5,217,010 A | 6/1993 | Tsitlik et al. |
| 5,222,506 A | 6/1993 | Patrick et al. |
| 5,231,996 A | 8/1993 | Bardy et al. |
| 5,241,957 A | 9/1993 | Camp et al. |
| 5,243,911 A | 9/1993 | Dow et al. |
| 5,246,014 A | 9/1993 | Williams et al. |
| 5,259,395 A | 11/1993 | Li |
| 5,300,108 A | 4/1994 | Rebell et al. |
| 5,324,322 A | 6/1994 | Grill, Jr. et al. |
| 5,330,522 A | 7/1994 | Kreyenhagen |
| 5,354,327 A | 10/1994 | Smits |
| 5,370,666 A | 12/1994 | Lindberg et al. |
| 5,378,234 A | 1/1995 | Hammerslag et al. |
| 5,387,199 A | 2/1995 | Siman et al. |
| 5,417,208 A | 5/1995 | Winkler |
| 5,425,755 A | 6/1995 | Doan |
| 5,456,707 A | 10/1995 | Giele |
| 5,476,485 A | 12/1995 | Weinberg et al. |
| 5,483,022 A | 1/1996 | Mar |
| 5,522,872 A | 6/1996 | Hoff |
| 5,522,875 A | 6/1996 | Gates et al. |
| 5,534,018 A | 7/1996 | Wahlstrand et al. |
| 5,542,173 A | 8/1996 | Mar et al. |
| 5,542,174 A | 8/1996 | Chiu |
| 5,545,205 A | 8/1996 | Schulte et al. |
| 5,549,646 A | 8/1996 | Katz et al. |
| 5,554,139 A | 9/1996 | Okajima |
| 5,574,249 A | 11/1996 | Lindsay |
| 5,584,873 A | 12/1996 | Shoberg et al. |
| 5,599,576 A | 2/1997 | Opolski |
| 5,609,622 A | 3/1997 | Soukup et al. |
| 5,618,208 A | 4/1997 | Crouse et al. |
| 5,649,974 A | 7/1997 | Nelson et al. |
| 5,658,709 A | 8/1997 | Layman et al. |
| 5,676,694 A | 10/1997 | Boser et al. |
| 5,727,552 A | 3/1998 | Ryan |
| 5,727,553 A | 3/1998 | Saad |
| 5,728,149 A | 3/1998 | Laske et al. |
| 5,755,742 A | 5/1998 | Schuelke et al. |
| 5,760,341 A | 6/1998 | Laske et al. |
| 5,766,227 A | 6/1998 | Nappholz et al. |
| 5,800,496 A | 9/1998 | Swoyer et al. |
| 5,810,887 A | 9/1998 | Accorti, Jr. et al. |
| 5,817,136 A | 10/1998 | Nappholz et al. |
| 5,824,026 A | 10/1998 | Diaz |
| 5,833,715 A | 11/1998 | Vachon et al. |
| 5,849,031 A | 12/1998 | Martinez et al. |
| 5,891,114 A | 4/1999 | Thomas et al. |
| 5,891,179 A | 4/1999 | Er et al. |
| 5,935,159 A | 8/1999 | Cross, Jr. et al. |
| 5,957,966 A | 9/1999 | Schroeppel et al. |
| 5,957,970 A | 9/1999 | Shoberg et al. |
| 5,968,087 A | 10/1999 | Hess et al. |
| 6,016,447 A | 1/2000 | Juran et al. |
| 6,057,031 A | 5/2000 | Breme et al. |
| 6,078,840 A | 6/2000 | Stokes |
| 6,083,216 A | 7/2000 | Fischer, Sr. |
| 6,101,417 A | 8/2000 | Vogel et al. |
| 6,106,522 A | 8/2000 | Fleischman et al. |
| 6,141,593 A | 10/2000 | Patag |
| 6,143,013 A | 11/2000 | Samson et al. |
| 6,178,355 B1 | 1/2001 | Williams et al. |
| 6,192,280 B1 | 2/2001 | Sommer et al. |
| 6,208,881 B1 | 3/2001 | Champeau |
| 6,249,708 B1 | 6/2001 | Nelson et al. |
| 6,256,541 B1 | 7/2001 | Heil et al. |
| 6,259,954 B1 | 7/2001 | Conger et al. |
| 6,289,250 B1 | 9/2001 | Tsuboi et al. |
| 6,295,476 B1 | 9/2001 | Schaenzer |
| 6,304,784 B1 | 10/2001 | Allee et al. |
| 6,317,633 B1 | 11/2001 | Jorgenson et al. |
| 6,356,790 B1 | 3/2002 | Maguire et al. |
| 6,360,129 B1 | 3/2002 | Ley et al. |
| 6,400,992 B1 | 6/2002 | Borgersen et al. |
| 6,428,537 B1 | 8/2002 | Swanson et al. |
| 6,434,430 B2 | 8/2002 | Borgersen et al. |
| 6,456,888 B1 | 9/2002 | Skinner et al. |
| 6,493,591 B1 | 12/2002 | Stokes |
| 6,501,991 B1 | 12/2002 | Honeck et al. |
| 6,501,994 B1 | 12/2002 | Janke et al. |
| 6,510,345 B1 | 1/2003 | Van Bentem |
| 6,516,230 B2 | 2/2003 | Williams et al. |
| 6,526,321 B1 | 2/2003 | Spehr |
| 6,564,107 B1 | 5/2003 | Bodner et al. |
| 6,671,554 B2 | 12/2003 | Gibson et al. |
| 6,701,191 B2 | 3/2004 | Schell |
| 6,721,600 B2 | 4/2004 | Jorgenson et al. |
| 6,721,604 B1 | 4/2004 | Robinson et al. |
| 6,813,251 B1 | 11/2004 | Garney et al. |
| 6,813,521 B2 | 11/2004 | Bischoff et al. |
| 6,850,803 B1 | 2/2005 | Jimenez et al. |
| 6,854,994 B2 | 2/2005 | Stein et al. |
| 6,866,044 B2 | 3/2005 | Bardy et al. |
| 6,906,256 B1 | 6/2005 | Wang |
| 6,920,361 B2 | 7/2005 | Williams |
| 6,925,334 B1 | 8/2005 | Salys |
| 6,944,489 B2 | 9/2005 | Zeijlemaker et al. |
| 6,949,929 B2 | 9/2005 | Gray et al. |
| 6,978,185 B2 | 12/2005 | Osypka |
| 6,985,755 B2 | 1/2006 | Cadieux et al. |
| 6,985,775 B2 | 1/2006 | Reinke et al. |
| 6,993,373 B2 | 1/2006 | Vrijheid et al. |
| 6,999,818 B2 | 2/2006 | Stevenson et al. |
| 6,999,821 B2 | 2/2006 | Jenney et al. |
| 7,013,180 B2 | 3/2006 | Dublin et al. |
| 7,013,182 B1 | 3/2006 | Krishnan |
| 7,047,075 B2 | 5/2006 | Stubbs |
| 7,047,083 B2 | 5/2006 | Gunderson et al. |
| 7,050,855 B2 | 5/2006 | Zeijlemaker et al. |
| 7,113,827 B2 | 9/2006 | Silvestri et al. |
| 7,123,013 B2 | 10/2006 | Gray |
| 7,127,294 B1 | 10/2006 | Wang et al. |
| 7,135,978 B2 | 11/2006 | Gisselberg et al. |
| 7,138,582 B2 | 11/2006 | Lessar et al. |
| 7,158,837 B2 | 1/2007 | Osypka et al. |
| 7,174,219 B2 | 2/2007 | Wahlstrand et al. |
| 7,174,220 B1 | 2/2007 | Chitre et al. |
| 7,205,768 B2 | 4/2007 | Schulz et al. |
| 7,239,916 B2 | 7/2007 | Thompson et al. |
| 7,242,987 B2 | 7/2007 | Holleman et al. |
| 7,257,449 B2 | 8/2007 | Bodner |
| 7,289,851 B2 | 10/2007 | Gunderson et al. |
| 7,363,090 B2 | 4/2008 | Halperin et al. |
| 7,369,898 B1 | 5/2008 | Kroll et al. |
| 7,378,931 B2 | 5/2008 | Odahara et al. |
| 7,388,378 B2 | 6/2008 | Gray et al. |
| 7,389,148 B1 | 6/2008 | Morgan |
| 7,453,344 B2 | 11/2008 | Maeda et al. |
| 7,535,363 B2 | 5/2009 | Gisselberg et al. |
| 7,571,010 B2 | 8/2009 | Zarembo et al. |
| 7,584,005 B1 | 9/2009 | Jain |
| 7,610,101 B2 | 10/2009 | Wedan et al. |
| 7,630,761 B2 | 12/2009 | Salo et al. |
| 7,689,291 B2 | 3/2010 | Polkinghorne et al. |
| 7,765,005 B2 | 7/2010 | Stevenson |
| 7,853,332 B2 | 12/2010 | Olsen et al. |

(56) References Cited

U.S. PATENT DOCUMENTS

| | | |
|---|---|---|
| 7,877,150 B2 | 1/2011 | Hoegh et al. |
| 7,912,552 B2 | 3/2011 | Przybyszewski |
| 7,917,213 B2 | 3/2011 | Bulkes et al. |
| 7,933,662 B2 | 4/2011 | Marshall et al. |
| 7,953,499 B2 | 5/2011 | Knapp et al. |
| 7,986,999 B2 | 7/2011 | Wedan et al. |
| 7,991,484 B1 | 8/2011 | Sengupta et al. |
| 8,000,801 B2 | 8/2011 | Stevenson et al. |
| 8,027,736 B2 | 9/2011 | Wahlstrand et al. |
| 8,032,230 B1 | 10/2011 | Cox et al. |
| 8,046,084 B2 | 10/2011 | Bodner |
| 8,099,177 B2 | 1/2012 | Dahlberg |
| 8,103,360 B2 | 1/2012 | Foster |
| 8,108,054 B2 | 1/2012 | Helland |
| 8,145,324 B1 | 3/2012 | Stevenson et al. |
| 8,170,688 B2 | 5/2012 | Wedan et al. |
| 8,200,342 B2 | 6/2012 | Stevenson et al. |
| 8,214,055 B2 | 7/2012 | Erickson |
| 8,244,346 B2 | 8/2012 | Foster et al. |
| 8,255,055 B2 | 8/2012 | Ameri |
| 8,315,715 B2 | 11/2012 | Erickson |
| 8,369,964 B2 | 2/2013 | Ameri |
| 8,391,994 B2 | 3/2013 | Foster et al. |
| 8,401,671 B2 | 3/2013 | Wedan et al. |
| 8,543,218 B2 | 9/2013 | Erickson |
| 8,666,508 B2 | 3/2014 | Foster et al. |
| 8,731,685 B2 | 5/2014 | Ameri |
| 8,744,600 B2 | 6/2014 | Perrey et al. |
| 9,203,648 B2 | 12/2015 | Shraim et al. |
| 9,254,380 B2 | 2/2016 | Ameri et al. |
| 2002/0065544 A1 | 5/2002 | Smits |
| 2002/0072769 A1 | 6/2002 | Silvian et al. |
| 2002/0111664 A1 | 8/2002 | Bartig et al. |
| 2002/0128689 A1 | 9/2002 | Connelly et al. |
| 2002/0144720 A1 | 10/2002 | Zahorik et al. |
| 2003/0028231 A1 | 2/2003 | Partridge et al. |
| 2003/0050680 A1 | 3/2003 | Gibson et al. |
| 2003/0063946 A1 | 4/2003 | Williams et al. |
| 2003/0083723 A1 | 5/2003 | Wilkinson et al. |
| 2003/0083726 A1 | 5/2003 | Zeijlemaker et al. |
| 2003/0092303 A1 | 5/2003 | Osypka |
| 2003/0093136 A1 | 5/2003 | Osypka et al. |
| 2003/0093138 A1 | 5/2003 | Osypka et al. |
| 2003/0139794 A1 | 7/2003 | Jenney et al. |
| 2003/0140931 A1 | 7/2003 | Zeijlemaker et al. |
| 2003/0144705 A1 | 7/2003 | Funke |
| 2003/0144716 A1 | 7/2003 | Reinke et al. |
| 2003/0144718 A1 | 7/2003 | Zeijlemaker |
| 2003/0144719 A1 | 7/2003 | Zeijlemaker |
| 2003/0144720 A1 | 7/2003 | Villaseca et al. |
| 2003/0144721 A1 | 7/2003 | Villaseca et al. |
| 2003/0204217 A1 | 10/2003 | Greatbatch |
| 2004/0014355 A1 | 1/2004 | Osypka et al. |
| 2004/0064161 A1 | 4/2004 | Gunderson et al. |
| 2004/0064173 A1 | 4/2004 | Hine et al. |
| 2004/0064174 A1 | 4/2004 | Belden |
| 2004/0088033 A1 | 5/2004 | Smits et al. |
| 2004/0097965 A1 | 5/2004 | Gardeski et al. |
| 2004/0122490 A1 | 6/2004 | Reinke et al. |
| 2004/0153049 A1 | 8/2004 | Hewitt et al. |
| 2004/0162600 A1 | 8/2004 | Williams |
| 2004/0167442 A1 | 8/2004 | Shireman et al. |
| 2004/0172117 A1 | 9/2004 | Hill et al. |
| 2004/0193140 A1 | 9/2004 | Griffin et al. |
| 2004/0243210 A1 | 12/2004 | Morgan et al. |
| 2004/0267107 A1 | 12/2004 | Lessar et al. |
| 2005/0030322 A1 | 2/2005 | Gardos |
| 2005/0070972 A1 | 3/2005 | Wahlstrand et al. |
| 2005/0090886 A1 | 4/2005 | MacDonald et al. |
| 2005/0113676 A1 | 5/2005 | Weiner et al. |
| 2005/0113873 A1 | 5/2005 | Weiner et al. |
| 2005/0113876 A1 | 5/2005 | Weiner et al. |
| 2005/0136385 A1 | 6/2005 | Mann et al. |
| 2005/0149169 A1 | 7/2005 | Wang et al. |
| 2005/0177135 A1 | 8/2005 | Hildebrand et al. |
| 2005/0182471 A1 | 8/2005 | Wang |
| 2005/0197677 A1 | 9/2005 | Stevenson |
| 2005/0222642 A1 | 10/2005 | Przybyszewski et al. |
| 2005/0222656 A1 | 10/2005 | Wahlstrand et al. |
| 2005/0222657 A1 | 10/2005 | Wahlstrand et al. |
| 2005/0222658 A1 | 10/2005 | Hoegh et al. |
| 2005/0222659 A1 | 10/2005 | Olsen et al. |
| 2005/0227398 A1 | 10/2005 | Anderson et al. |
| 2005/0246007 A1 | 11/2005 | Sommer et al. |
| 2005/0267556 A1 | 12/2005 | Shuros et al. |
| 2005/0272280 A1 | 12/2005 | Osypka |
| 2005/0283167 A1 | 12/2005 | Gray |
| 2006/0009819 A1 | 1/2006 | Przybyszewski |
| 2006/0030774 A1 | 2/2006 | Gray et al. |
| 2006/0037461 A1 | 2/2006 | Yasumura |
| 2006/0041293 A1 | 2/2006 | Mehdizadeh et al. |
| 2006/0041294 A1 | 2/2006 | Gray |
| 2006/0041296 A1 | 2/2006 | Bauer et al. |
| 2006/0089691 A1 | 4/2006 | Kaplan et al. |
| 2006/0089695 A1 | 4/2006 | Bolea et al. |
| 2006/0089696 A1 | 4/2006 | Olsen et al. |
| 2006/0093685 A1 | 5/2006 | Mower et al. |
| 2006/0105066 A1 | 5/2006 | Teague et al. |
| 2006/0106442 A1 | 5/2006 | Richardson et al. |
| 2006/0118758 A1 | 6/2006 | Wang et al. |
| 2006/0129043 A1 | 6/2006 | Ben-Jacob et al. |
| 2006/0167536 A1 | 7/2006 | Nygren et al. |
| 2006/0200218 A1 | 9/2006 | Wahlstrand |
| 2006/0229693 A1 | 10/2006 | Bauer et al. |
| 2006/0247747 A1 | 11/2006 | Olsen et al. |
| 2006/0247748 A1 | 11/2006 | Wahlstrand et al. |
| 2006/0252314 A1 | 11/2006 | Atalar et al. |
| 2006/0253180 A1 | 11/2006 | Zarembo et al. |
| 2006/0271138 A1 | 11/2006 | MacDonald |
| 2006/0293737 A1 | 12/2006 | Krishnan |
| 2007/0010702 A1 | 1/2007 | Wang et al. |
| 2007/0027532 A1 | 2/2007 | Wang et al. |
| 2007/0055317 A1 | 3/2007 | Stahmann et al. |
| 2007/0106332 A1 | 5/2007 | Denker et al. |
| 2007/0112398 A1 | 5/2007 | Stevenson et al. |
| 2007/0156205 A1 | 7/2007 | Larson et al. |
| 2007/0179577 A1 | 8/2007 | Marshall et al. |
| 2007/0179582 A1 | 8/2007 | Marshall et al. |
| 2007/0191914 A1 | 8/2007 | Stessman |
| 2007/0208383 A1 | 9/2007 | Williams |
| 2007/0255317 A1 | 11/2007 | Fanton et al. |
| 2007/0255378 A1 | 11/2007 | Polkinghorne et al. |
| 2008/0009905 A1 | 1/2008 | Zeijlemaker |
| 2008/0033497 A1 | 2/2008 | Bulkes et al. |
| 2008/0039709 A1 | 2/2008 | Karmarkar |
| 2008/0049376 A1 | 2/2008 | Stevenson et al. |
| 2008/0051854 A1 | 2/2008 | Bulkes et al. |
| 2008/0057784 A1 | 3/2008 | Zarembo et al. |
| 2008/0058902 A1 | 3/2008 | Gray et al. |
| 2008/0119917 A1 | 5/2008 | Geistert |
| 2008/0125754 A1 | 5/2008 | Beer et al. |
| 2008/0129435 A1 | 6/2008 | Gray |
| 2008/0132985 A1 | 6/2008 | Wedan et al. |
| 2008/0132986 A1 | 6/2008 | Gray et al. |
| 2008/0140152 A1 | 6/2008 | Imran et al. |
| 2008/0154348 A1 | 6/2008 | Atalar et al. |
| 2008/0208290 A1 | 8/2008 | Phillips et al. |
| 2008/0243218 A1 | 10/2008 | Bottomley et al. |
| 2008/0262584 A1* | 10/2008 | Bottomley et al. ........... 607/119 |
| 2008/0269831 A1 | 10/2008 | Erickson |
| 2009/0005825 A1 | 1/2009 | MacDonald |
| 2009/0024180 A1 | 1/2009 | Kisker et al. |
| 2009/0024197 A1 | 1/2009 | Jensen |
| 2009/0099440 A1 | 4/2009 | Viohl |
| 2009/0099555 A1 | 4/2009 | Viohl et al. |
| 2009/0118610 A1 | 5/2009 | Karmarkar et al. |
| 2009/0149920 A1 | 6/2009 | Li et al. |
| 2009/0149933 A1 | 6/2009 | Ameri |
| 2009/0149934 A1 | 6/2009 | Ameri et al. |
| 2009/0198314 A1 | 8/2009 | Foster et al. |
| 2009/0204171 A1 | 8/2009 | Ameri |
| 2009/0210022 A1 | 8/2009 | Powers |
| 2009/0270948 A1 | 10/2009 | Nghiem et al. |
| 2009/0270956 A1 | 10/2009 | Vase et al. |

(56) References Cited

U.S. PATENT DOCUMENTS

| | | |
|---|---|---|
| 2009/0281608 A1 | 11/2009 | Foster |
| 2010/0010602 A1 | 1/2010 | Wedan et al. |
| 2010/0016935 A1 | 1/2010 | Strandberg et al. |
| 2010/0049290 A1 | 2/2010 | Min et al. |
| 2010/0103215 A1 | 4/2010 | Iriguchi |
| 2010/0106215 A1 | 4/2010 | Stubbs et al. |
| 2010/0114277 A1 | 5/2010 | Zhao et al. |
| 2010/0125320 A1 | 5/2010 | Polkinghorne et al. |
| 2010/0137928 A1 | 6/2010 | Duncan et al. |
| 2010/0174348 A1 | 7/2010 | Bulkes et al. |
| 2010/0174349 A1 | 7/2010 | Stevenson et al. |
| 2010/0234929 A1 | 9/2010 | Scheuermann |
| 2010/0249892 A1 | 9/2010 | Bulkes et al. |
| 2010/0292744 A1 | 11/2010 | Hill et al. |
| 2010/0331936 A1 | 12/2010 | Perrey et al. |
| 2011/0060394 A1 | 3/2011 | Poore |
| 2011/0079423 A1 | 4/2011 | Zhao et al. |
| 2011/0087299 A1 | 4/2011 | Ameri |
| 2011/0087302 A1 | 4/2011 | Ameri |
| 2011/0093054 A1 | 4/2011 | Ameri |
| 2011/0160817 A1 | 6/2011 | Foster et al. |
| 2011/0160828 A1 | 6/2011 | Foster et al. |
| 2011/0160829 A1 | 6/2011 | Foster et al. |
| 2011/0208280 A1 | 8/2011 | Li et al. |
| 2011/0218422 A1 | 9/2011 | Atalar et al. |
| 2011/0238146 A1 | 9/2011 | Wedan et al. |
| 2011/0288403 A1 | 11/2011 | Kondabatni et al. |
| 2012/0016451 A1 | 1/2012 | Struve et al. |
| 2012/0022356 A1 | 1/2012 | Olsen et al. |
| 2012/0035698 A1 | 2/2012 | Johnson et al. |
| 2012/0053662 A1 | 3/2012 | Foster et al. |
| 2012/0109270 A1 | 5/2012 | Foster |
| 2012/0161901 A1 | 6/2012 | Stevenson et al. |
| 2012/0179233 A1 | 7/2012 | Wedan et al. |
| 2012/0253340 A1 | 10/2012 | Stevenson et al. |
| 2012/0271394 A1 | 10/2012 | Foster et al. |
| 2013/0123884 A1 | 5/2013 | Ameri |
| 2013/0190849 A1 | 7/2013 | Perrey et al. |
| 2013/0190850 A1 | 7/2013 | Wedan et al. |

FOREIGN PATENT DOCUMENTS

| | | |
|---|---|---|
| CN | 1905789 A | 1/2007 |
| CN | 101039619 A | 9/2007 |
| CN | 101553165 B | 10/2009 |
| CN | 102186534 A | 9/2011 |
| CN | 102209575 A | 10/2011 |
| EP | 0897997 B1 | 2/2003 |
| EP | 1594564 A1 | 11/2005 |
| EP | 1852810 B1 | 11/2007 |
| EP | 2445577 B1 | 5/2012 |
| EP | 2227289 B1 | 7/2015 |
| JP | H0747139 A | 2/1995 |
| JP | 2001522631 A | 11/2001 |
| JP | 2004511293 A | 4/2004 |
| JP | 2004141679 A | 5/2004 |
| JP | 2005501673 A | 1/2005 |
| JP | 2005515852 A | 6/2005 |
| JP | 2005515854 A | 6/2005 |
| JP | 2005522301 A | 7/2005 |
| JP | 2007520254 A | 7/2007 |
| JP | 2011504405 A | 2/2011 |
| JP | 2011505182 A | 2/2011 |
| JP | 2011509813 A | 3/2011 |
| WO | WO9606655 A1 | 3/1996 |
| WO | WO9923958 A1 | 5/1999 |
| WO | WO0232325 A1 | 4/2002 |
| WO | WO03063946 A2 | 8/2003 |
| WO | WO03063953 A2 | 8/2003 |
| WO | WO03089045 A2 | 10/2003 |
| WO | WO2004073791 A1 | 9/2004 |
| WO | WO2005030322 A1 | 4/2005 |
| WO | WO2006105066 A2 | 3/2006 |
| WO | WO2006093685 A1 | 9/2006 |
| WO | WO2007047966 A2 | 4/2007 |
| WO | WO2007089986 A1 | 8/2007 |
| WO | WO2007118194 A2 | 10/2007 |
| WO | WO2008051122 A1 | 5/2008 |
| WO | WO2009100003 A1 | 8/2009 |
| WO | WO20090137186 A1 | 11/2009 |
| WO | WO2010078552 A1 | 7/2010 |

OTHER PUBLICATIONS

International Search Report and Written Opinion issued in PCT/US2010/055130, mailed Mar. 10, 2011, 11 pages.

Gray, Robert W. et al., "Simple design changes to wires to substantially reduce MRI-induced heating at 1.5 T: implications for implanted leads", Magnetic Resonance Imaging 23 (2005) 887-891.

International Search Report and Written Opinion issued in PCT/US2008/085518 on Oct. 29, 2009, 15 pages.

International Search Report and Written Opinion issued in PCT/US2009/032838, mailed May 4, 2009, 14 pages.

International Search Report and Written Opinion issued in PCT/US2009/038629, mailed Jun. 29, 2009, 11 pages.

International Search Report and Written Opinion issued in PCT/US2010/024062, mailed Sep. 27, 2010.

International Search Report and Written Opinion issued in PCT/US2010/033686 on Aug. 10, 2010, 12 pages.

Invitation to Pay Additional Fees and Partial Search Report, dated Aug. 17, 2009, issued in PCT/US2008/085533, 6 pages.

Invitation to Pay Additional Fees and Partial Search Report, issued in PCT/US2010/024062, mailed May 7, 2010.

International Search Report and Written Opinion issued in PCT/US2012/055673, mailed Dec. 13, 2012, 10 pages.

International Search Report and Written Opinion issued in PCT/US2013/065517, dated Dec. 20, 2013, 11 pgs.

"High Voltage Engineering and Testing, 2nd Edition", edited by Hugh M. Ryan, Institution of Engineering and Technology, 2001, 15 pages.

Avalanche Breakdown, Wikipedia Article, captured Apr. 6, 2010, [http://en.wikipedia.org/wiki/Avalanche_breakdown].

Basso, Christophe, "SPICE Model Simulates Spark-Gap Arrestor", Electronics Design, Strategy, and News (EDN), Jul. 3, 1997, 4 pages.

Citel Inc., Data Sheet, BH Series 2 Electrode Miniature Gas Discharge Tube Surge Arrester—8mm, May 14, 2009, 2 pages.

File History for U.S. Appl. No. 11/015,807, filed Dec. 17, 2004 to Cooke, Daniel J. et al.

Hayes, David L., Chapter 4, "Generator and Lead Selection" from book entitled "Cardiac Pacing and Defibrillation A Clinical Approach", John Wiley & Sons, (c) 2000 Mayo Foundation, p. 129-157.

International Preliminary Examination Report issued in PCT/US2013/065517, dated Apr. 21, 2015, 8 pages.

International Preliminary Report on Patentability issued in PCT/US2015/017473, dated Sep. 9, 2016, 8 pages.

International Search Report and Written Opinion issued in PCT/US2009/056843, dated Dec. 29, 2009, 13 pages.

International Search Report and Written Opinion issued in PCT/US2010/048620, dated Apr. 5, 2011, 10 pages.

International Search Report and Written Opinion issued in PCT/US2010/053223, dated Dec. 27, 2010, 11 pages.

International Search Report and Written Opinion issued in PCT/US2011/052541, dated Mar. 9, 2012, 22 pages.

International Search Report and Written Opinion issued in PCT/US2013/037432, dated Nov. 19, 2013, 17 pages.

International Search Report and Written Opinion issued in PCT/US2013/057732, dated Dec. 13, 2013, 11 pages.

International Search Report and Written Opinion issued in PCT/US2015/017473, dated May 20, 2015, 10 pages.

Partial International Search Report issued in PCT/US2011/052541, dated Dec. 6, 2011, 4 pages.

Partial International Search Report issued in PCT/US2013/037432, dated Jul. 17, 2013, 6 pages.

Static Spark Gap Analysis, captured Dec. 24, 2002, [http://www.richieburnett.co.uk/static.html].

(56) References Cited

OTHER PUBLICATIONS

Third Party Submission Under 37 CFR 1.290 filed in U.S. Appl. No. 14/056,746 dated May 20, 2014, 13 pages.

* cited by examiner

MRI-CONDITIONALLY SAFE MEDICAL DEVICE LEAD

CROSS-REFERENCE TO RELATED APPLICATION

This application claims priority to Provisional Application No. 61/291,076, filed Dec. 30, 2009, which is herein incorporated by reference in its entirety.

TECHNICAL FIELD

The present invention relates to implantable medical devices. More particularly, the present invention relates to an implantable medical device lead including an inner conductor having a layered coil arrangement and an outer coil.

BACKGROUND

Magnetic resonance imaging (MRI) is a non-invasive imaging procedure that utilizes nuclear magnetic resonance techniques to render images within a patient's body. Typically, MRI systems employ the use of a magnetic coil having a magnetic field strength of between about 0.2 to 3 Teslas. During the procedure, the body tissue is briefly exposed to RF pulses of electromagnetic energy in a plane perpendicular to the magnetic field. The resultant electromagnetic energy from these pulses can be used to image the body tissue by measuring the relaxation properties of the excited atomic nuclei in the tissue.

During imaging, the electromagnetic radiation produced by the MRI system may be picked up by implantable device leads used in implantable medical devices such as pacemakers or cardiac defibrillators. This energy may be transferred through the lead to the electrode in contact with the tissue, which may lead to elevated temperatures at the point of contact. The degree of tissue heating is typically related to factors such as the length of the lead, the conductivity or impedance of the lead, and the surface area of the lead electrodes. Exposure to a magnetic field may also induce an undesired voltage on the lead.

SUMMARY

Discussed herein are various conductor configurations for implantable medical electrical leads including an outer conductive coil extending coaxially with an inner multi-layer conductor assembly, as well as medical electrical leads including such conductor configurations.

In Example 1, an implantable medical device lead comprises an inner conductor assembly coupled to a first electrode at a distal end of the inner conductor assembly, and an outer conductive coil extending coaxially with the inner conductor assembly and coupled to a second electrode. The inner conductor assembly includes one or more filars arranged in a plurality of serially connected current suppression modules. Each current suppression module includes a first coil of the one or more filars wound in a first winding direction, a second coil of the one or more filars coaxial with the first winding and wound in a second winding direction opposite the first winding direction, and a third coil of the one or more filars coaxial with the first and second windings and wound in the first winding direction. The outer conductive coil is wound in the first winding direction.

In Example 2, the implantable medical device lead according to Example 1, wherein the outer conductive coil comprises two or fewer filars each having a filar diameter, and wherein a pitch of the outer conductive coil is less than three times the filar diameter.

In Example 3, the implantable medical device lead according to either Example 1 or 2, wherein the outer conductive coil comprises a single filar, and wherein the pitch of the outer conductive coil is less than two times the filar diameter.

In Example 4, the implantable medical device lead according to any of Examples 1-3, wherein each current suppression module has a length of between about 1.5 cm and 10 cm.

In Example 5, the implantable medical device lead according to any of Examples 1-4, wherein the inner conductor assembly comprises four filars.

In Example 6, the implantable medical device lead according to any of Examples 1-5, and further comprising an insulative layer between the inner conductor assembly and the outer conductive coil.

In Example 7, a medical device comprises a pulse generator, a lead including a lead body, an outer conductive coil extending through the lead body, and an inner conductor assembly extending coaxially with the outer conductive coil. The inner conductor assembly is coupled to a first electrode at a distal end of the inner conductor assembly and includes one or more filars arranged in a plurality of serially connected current suppression modules. Each current suppression module includes a first coil of the one or more filars wound in a first winding direction, a second coil of the one or more filars coaxial with the first winding and wound in a second winding direction opposite the first winding direction, and a third coil of the one or more filars coaxial with the first and second windings and wound in the first winding direction. The outer conductive coil is coupled to a second electrode and includes one or more filars wound in the first winding direction.

In Example 8, the medical device according to Example 7, wherein the outer conductive coil comprises two or fewer filars each having a filar diameter, and wherein a pitch of the outer conductive coil is less than three times the filar diameter.

In Example 9, the medical device according to either Example 7 or 8, wherein the outer conductive coil comprises a single filar, and wherein the pitch of the outer conductive coil is less than two times the filar diameter.

In Example 10, the medical device according to any of Examples 7-9, wherein each current suppression module has a length of between about 1.5 cm and 10 cm.

In Example 11, the medical device according to any of Examples 7-10, wherein the inner conductor assembly comprises four filars.

In Example 12, the medical device according to any of Examples 7-11, and further comprising an insulative layer between the inner conductor assembly and the outer conductive coil.

In Example 13, an implantable medical device lead comprises an insulative lead body, an outer conductive coil, and an inner conductor assembly. The outer conductive coil extends through the lead body, is coupled to a proximal electrode, and includes one or more filars wound in a first winding direction. The inner conductor assembly extends coaxially with the outer conductive coil and is coupled to a distal electrode at a distal end of the inner conductor assembly. The inner conductor assembly includes one or more filars arranged in a plurality of serially connected current suppression modules. Each current suppression module includes a multi-layer coil configuration with the one or more filars wound in a first coiled section having a first winding direction and extending in a forward lengthwise direction for a first forward physical length. The one or more filars then turn to merge into a proximately positioned second coiled section wound in a second winding direction opposite the first winding direction that extends in a substantially opposing reverse lengthwise direction for a reverse physical length. The one or more filars then turn to merge into a proximately positioned third coiled section wound in the first winding direction that extends in the forward lengthwise direction for a second forward physical length.

In Example 14, the implantable medical device lead according to Example 13, wherein the outer conductive coil comprises a two or fewer filars each having a filar diameter, and wherein a pitch of the outer conductive coil is less than three times the filar diameter.

In Example 15, the implantable medical device lead according to either Example 13 or 14, wherein the outer conductive coil comprises a single filar, and wherein the pitch of the outer conductive coil is less than two times the filar diameter.

In Example 16, the implantable medical device lead according to any of Examples 13-15, wherein each current suppression module has a length of between about 1.5 cm and 10 cm.

In Example 17, the implantable medical device lead according to any of Examples 13-16, wherein the inner conductor assembly comprises four filars.

In Example 18, the implantable medical device lead according to any of Examples 13-17, and further comprising an insulative layer between the inner conductor assembly and the outer conductive coil.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
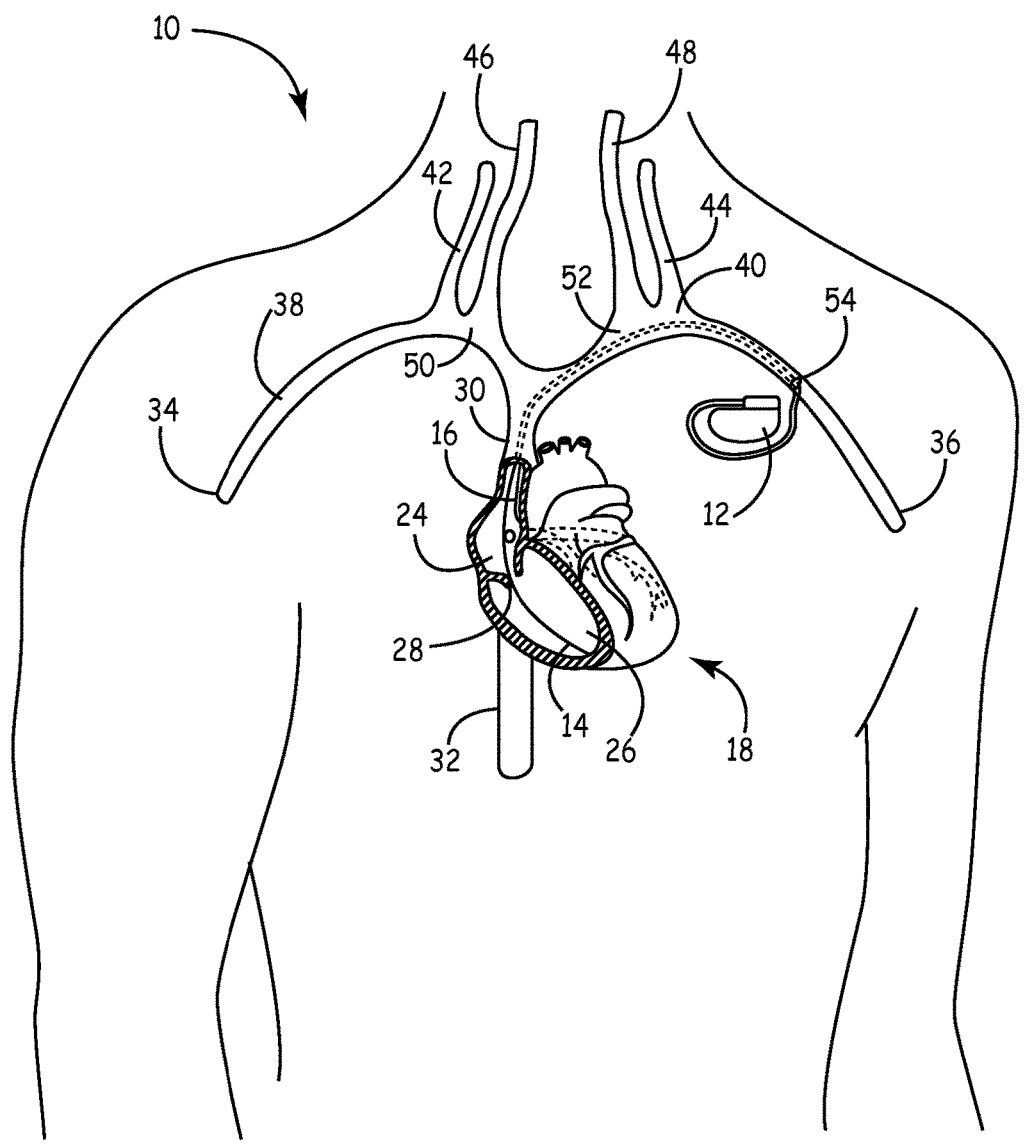
FIG. 1 is a schematic view of a cardiac rhythm management (CRM) system including a pulse generator and a lead implanted in a patient's heart according to an embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic view of a cardiac rhythm management (CRM) system 10 according to an embodiment of the present invention. As shown in FIG. 1, the CRM system 10 includes a pulse generator 12 coupled to a plurality of leads 14, 16 deployed in a patient's heart 18. As further shown in FIG. 1, the heart 18 includes a right atrium 24 and a right ventricle 26 separated by a tricuspid valve 28. During normal operation of the heart 18, deoxygenated blood is fed into the right atrium 24 through the superior vena cava 30 and the inferior vena cava 32. The major veins supplying blood to the superior vena cava 30 include the right and left axillary veins 34 and 36, which flow into the right and left subclavian veins 38 and 40. The right and left external jugular 42 and 44, along with the right and left internal jugular 46 and 48, join the right and left subclavian veins 38 and 40 to form the right and left brachiocephalic veins 50 and 52, which in turn combine to flow into the superior vena cava 30.

The leads 14, 16 operate to convey electrical signals and stimuli between the heart 18 and the pulse generator 12. In the illustrated embodiment, the lead 14 is implanted in the right ventricle 26, and the lead 16 is implanted in the right atrium 24. In other embodiments, the CRM system 10 may include additional leads, e.g., a lead extending into a coronary vein for stimulating the left ventricle in a bi-ventricular pacing or cardiac resynchronization therapy system. As shown, the leads 14, 16 enter the vascular system through a vascular entry site 54 formed in the wall of the left subclavian vein 40, extend through the left brachiocephalic vein 52 and the superior vena cava 30, and are implanted in the right ventricle 26 and right atrium 24, respectively. In other embodiments of the present invention, the leads 14, 16 may enter the vascular system through the right subclavian vein 38, the left axillary vein 36, the left external jugular 44, the left internal jugular 48, or the left brachiocephalic vein 52.

The pulse generator 12 is typically implanted subcutaneously within an implantation location or pocket in the patient's chest or abdomen. The pulse generator 12 may be any implantable medical device known in the art or later developed, for delivering an electrical therapeutic stimulus to the patient. In various embodiments, the pulse generator 12 is a pacemaker, an implantable cardiac defibrillator, and/or includes both pacing and defibrillation capabilities. The portion of the leads 14, 16 extending from the pulse generator 12 to the vascular entry site 54 are also located subcutaneously or submuscularly. The leads 14, 16 are each connected to the pulse generator 12 via proximal connectors. Any excess lead length, i.e., length beyond that needed to reach from the pulse generator 12 location to the desired intracardiac implantation site, is generally coiled up in the subcutaneous pocket near the pulse generator 12.

The electrical signals and stimuli conveyed by the pulse generator 12 are carried to electrodes at the distal ends of leads 14, 16 by one or more conductors extending through the leads 14, 16. The one or more conductors are each electrically coupled to a connector suitable for interfacing with the pulse generator 12 at the proximal end of the leads 14, 16 and to one or more electrodes at the distal end. In an MRI environment, the electromagnetic radiation produced by the MRI system may be picked up by conductors of the leads 14, 16. This energy may be transferred through the leads 14, 16 to the electrode in contact with the tissue, which may lead to elevated temperatures at the point of contact. The present invention relates to a bipolar lead having an inner conductive assembly including a plurality of series connected current suppression modules that reduces heating due to MRI induced energy. The bipolar lead also includes an outer conductive coil configured to minimize the effect on the energy picked up by the inner conductive assembly.

Figure 2:
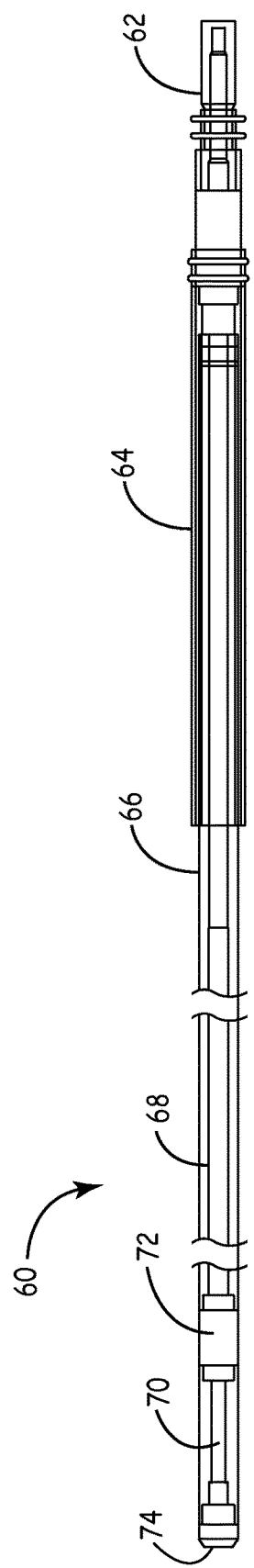
FIG. 2 is a side view of a lead suitable for use with the CRM system shown in FIG. 1.

FIG. 2 is a side view of a lead 60 that may be suitable for use with the CRM system 10 shown in FIG. 1. That is, the leads 14 and/or 16 shown in FIG. 1 may be configured similarly to the lead 60. The lead 60 includes a proximal connector 62, an insulative lead body 64, an outer conductive coil 66, an insulative layer 68, and an inner conductive assembly 70. As will be described in more detail below, the inner conductor assembly 70 is a multi-layer coil assembly that extends from a connector 62 at the proximal end of the lead 60 to one or more electrodes 72 at the distal end of the lead 60. The outer conductive coil 66 extends coaxially with the inner conductor assembly 70 and is electrically isolated from the inner conductor assembly 70 by the insulative layer 68. The outer conductive coil 66 is connected to the connector 62 at the proximal end of the lead 60 and to one or more electrodes 74 at the distal end of the lead 14. The insulative lead body 64 surrounds the outer conductive coil 66 and supports the one or more electrodes 72, 74 electrically coupled to a distal ends of the inner conductive assembly 70 and outer conductive coil 66, respectively. The connector 62 is configured to couple to the pulse generator 12 (FIG. 1) and electrically connects the electrodes 72, 74 to the pulse generator 12 via the inner conductor assembly 70 and outer conductive coil 66, respectively. The electrodes 72, 74 are merely illustrative, and may be configured for use in pacing, sensing, heart failure, and/or shock therapy applications. In addition, the electrode 74 may be configured for passive or active fixation of the lead 60 to tissue of the heart 18.

Figure 3:
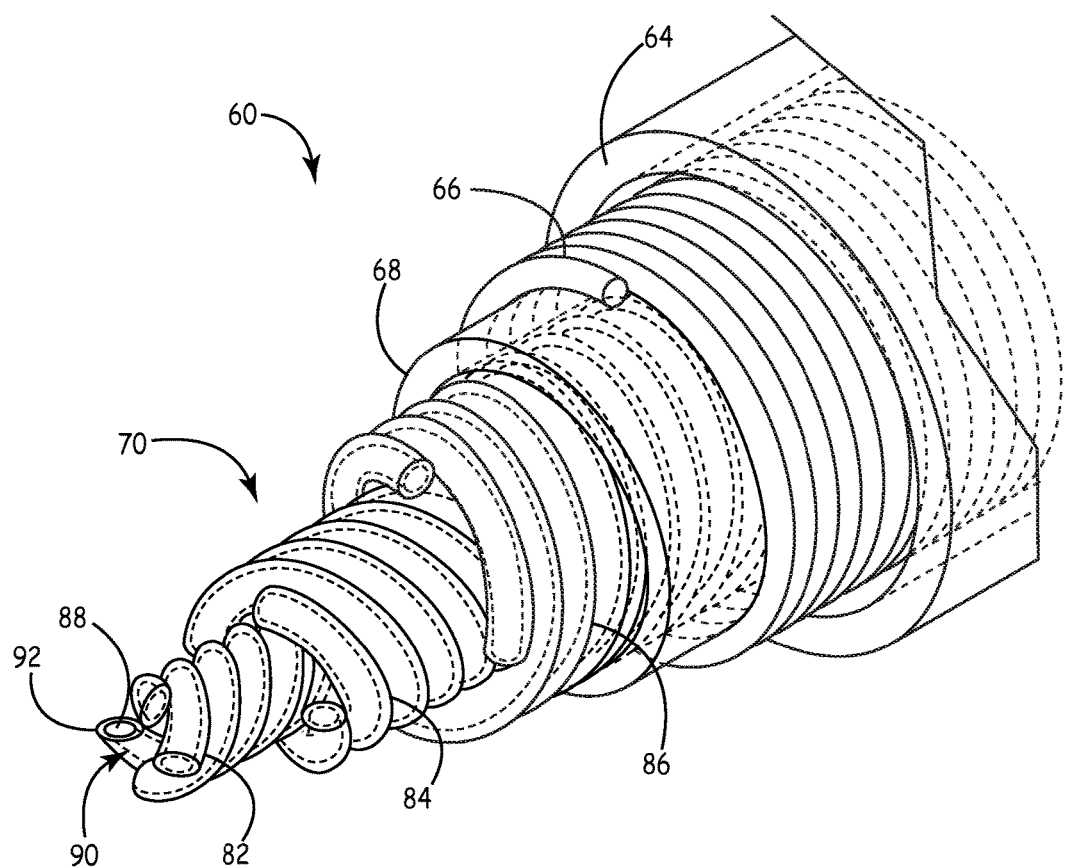
FIG. 3 is a perspective view of a lead portion including an embodiment of an inner conductive assembly and an outer coil extending coaxially with the inner conductive assembly.
Figure 4:
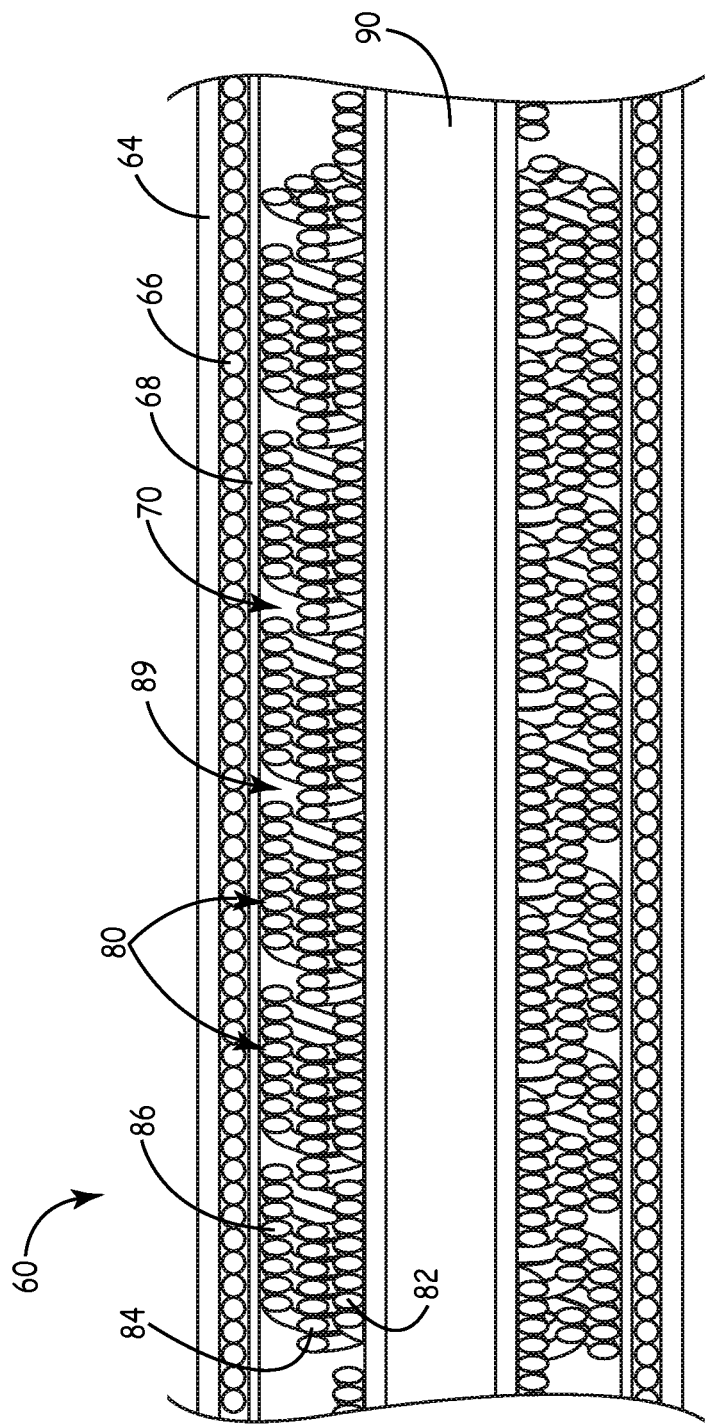
FIG. 4 is a cross-sectional view of the lead portion shown in FIG. 2, illustrating the series connected current suppression modules of the inner conductive assembly.

FIG. 3 is a perspective view and FIG. 4 is a cross-sectional view of an embodiment of the lead 60. The portion of the lead 60 shown in FIG. 3 has portions of each of the layers removed to illustrate each of the underlying layers. The inner conductor assembly 70 includes a plurality of series connected current suppression modules 80 that each include one or more filars wound into a multilayer coil assembly as will be described in more detail below. The segmented construction of the current suppression modules 80 prevent an MRI-induced RF standing wave from being generated on the inner conductor assembly 70. In addition, the arrangement of the filar(s) of the current suppression modules 80 cancels MRI-induced currents on the inner conductor assembly 70.

Each current suppression module 80 is an elongate conductor that turns back on itself at least twice in a lengthwise direction to form a conductor configuration of a reverse or backward section in one lengthwise direction and proximately located forward sections that extend in the opposing lengthwise direction. That is, the inner conductor assembly 70 is formed by winding the one or more filars into a plurality of multi-layer coiled configurations that each define a current suppression module 80. Each current suppression module 80 can be configured with a length that is a portion of the overall length of the inner conductor assembly 70. In some embodiments, the inner conductor assembly 70 is similar to the lead conductors including current suppression modules shown and described in U.S. Patent App. Pub. No. 2008/0262584, entitled "Methods and Apparatus for Fabricating Leads with Conductors and Related Flexible Lead Configurations," and U.S. Patent App. Pub. No. 2008/0243218, entitled "MRI and RF Compatible Leads and Related Methods of Operating and Fabricating Leads," each of which is hereby incorporated by reference in its entirety.

In some embodiments, each current suppression module 80 comprises a tri-layer configuration with three coiled segments closely stacked over each other, including an inner first coil 82, an intermediate second coil 84, and an outer third coil 86. The inner first coil 82 and outer third coil 86 are wound in a first, forward direction, and the inner second coil 84 is wound in a second, reverse direction. For example, in some embodiments, the inner first coil 82 and outer third coil 86 are wound in a left hand wind (i.e., right to left relative to a proximal to distal view of the lead 60), and the intermediate second coil 84 is wound in right hand wind (i.e., left to right relative to a proximal to distal view of the lead 60). In other embodiments, the inner first coil 82 and outer third coil 86 are wound in a right hand wind, and the intermediate second coil 84 is wound in a left hand wind.

The inner conductor assembly 70 is comprised of one or more filars 88 to form the plurality of current suppression modules 80 along the length of the inner conductor assembly 70. The filars 88 of the inner conductor assembly 70 are co-radially wound to form the inner first coil 82. The filars 88 are then wound back on themselves in the reverse direction to from the intermediate second coil 84 over the inner first coil 82. The filars 88 are then wound back on themselves again, reversing direction from the intermediate second coil 84 (i.e., in the same direction as the inner first coil 82), to form the outer third coil 86 over the intermediate second coil 84. The one or more filars 88 at the distal end of the outer third coil 86 then form a transition section 89 before forming the inner first coil 84 of the next current suppression module 80. In some embodiments, the current suppression modules 80 have a length in the longitudinal direction in the range of about 1.5 cm to about 10 cm., and the transition sections 89 have a length of between about 1.0 mm and about 3.0 mm. The length of each current suppression module 80 and transition section 89 can be controlled to optimize the current cancellation and segmentation in the inner conductor assembly 70. The current suppression modules 80 are arranged to define an inner lumen 90 and is suitable for receiving a tool to deliver the lead 60, such as a guidewire or stent.

Each of the coils 82, 84, and 86 can have a different pitch, or some or all of the coils 82, 84, and 86 can have the same pitch. In some embodiments, the inner first coil 82 can have a wider pitch and one or more of the overlying intermediate second coil 84 and outer third coil 86 can have a closer pitch.

In some embodiments, the inner conductor assembly 70 is comprised of 2-50 filars 88. In one exemplary implementation, the inner conductor assembly 70 comprises four filars 88. In some embodiments, the diameter of each filar is in the range of about 0.001 inch to 0.010 inch (0.003-0.025 cm). The filars may be comprised of a biocompatible materials, including, but not limited to, Au, Ag, Nitinol, Ti, Pt, Ir, MP35N, or stainless steel. The filars may also each include an insulation layer 92 of a biocompatible and dielectric material such as, for example, Teflon, Nylon, polymers, polytetrafluoroethylene (PTFE), ethylene tetrafluoroethylene (ETFE), silicone, polyurethane, poly ether ethyl ketone (PEEK), and/or epoxy. The thickness of the insulation layer 92 may be less than about 0.005 inch (0.01 cm). In some embodiments, the outside diameter of the inner conductive assembly 70 is less than about 0.10 inch (0.25 cm).

The outer conductive coil 66 is coaxially disposed about the inner conductor assembly 70 and has a helically coiled configuration that extends along all or a portion of the length of the lead 14. In some embodiments, the outer conductive coil 66 has a single-filar construction formed from a single wound wire. In other embodiments, the outer conductive coil 66 has a multifilar construction formed from multiple, co-radially wound wire filars. In one embodiment, for example, the outer conductive coil 66 has a double-filar construction formed from two co-radially wound wire filars.

The outer conductive coil 66 can be spaced radially apart from the inner conductor assembly 70, electrically isolating the outer conductive coil 66 from the inner conductor assembly 70. In some embodiments, for example, the outer conductive coil 66 is electrically isolated from the inner conductor assembly 70 so that the lead 14 can function as a multipolar lead. In certain embodiments, the insulative layer 68 is interposed between the inner conductor assembly 70 and the outer conductive coil 66 is further used to electrically isolate the inner conductor assembly 70 and outer conductive coil 66 from each other. In some embodiments, for example, the insulative layer 68 may comprise a sheath made from silicon, polyurethane, or other suitable polymeric material.

In some embodiments, the outer conductive coil 66 is formed from a drawn-filled tube having an outer tubular layer of low-resistive metal or metal-alloy filled with an inner core of electrically conductive material such as silver. Once filled and drawn, the tube is then coiled into a helical shape and attached to the lead 60 using conventional techniques known in the art. In use, the relatively low resistance of the outer tubular metal or metal-alloy forming part of the outer conductive coil 66 can be used to offset the increased resistance imparted to the outer conductive coil 66 from using a smaller diameter wire. In some embodiments, the material or materials forming the outer conductive coil 66 can also be selected so as to impart greater flexibility to the outer conductive coil 66.

The outer conductive coil 66 may be formed from a material or materials different than the inner conductor assembly 70 in order to increase the resistance of the outer conductive coil 66 to aid in dissipating RF electromagnetic energy received during an MRI procedure. In one embodiment, for example, the wire filar(s) forming the outer conductive coil 66 may comprise a silver-filled MP35N material having a silver content (by cross-sectional area) of about 28%, whereas the wire filar(s) forming the inner conductor assembly 70 may have a silver content (by cross-sectional area) lower than 28%. In some embodiments, the filar(s) of the outer conductive coil 66 are insulated. In other embodiments, the filar(s) of the outer conductive coil 66 are not insulated.

The outer conductive coil 66 is configured to minimize the interactions and effect on energy pickup with the inner conductor assembly 70 in an MRI environment, thereby minimizing the temperature increase at the distal electrode 74. In some embodiments, the outer conductive coil 66 is wound in the same direction as the inner first coil 82 and the outer third coil 86 to minimize the interaction between the outer conductive coil 66 and inner conductor assembly 70. For example, in embodiments in which the inner first coil 82 and outer third coil 86 are wound with a left hand wind, the outer conductive coil 66 is also wound in a left hand wind. As another example, in embodiments in which the inner first coil 82 and outer third coil 86 are wound with a right hand wind, the outer conductive coil 66 is also wound with a right hand wind.

The pitch of the outer conductive coil 66 may also be minimized (i.e., closely wound) to maximize the inductance of the outer conductive coil 66, thereby making the outer conductive coil 66 more resistant to excitation in MRI fields. For example, in double filar embodiments of the outer conductive coil 66, the pitch of the outer conductive coil 66 may be about two to three times the diameter of each of the filars. In single filar embodiments of the outer conductive coil 66, the pitch of the outer conductive coil 66 may be about one to two times the filar diameter.

To test the effect of the outer conductive coil 66 on heating at the electrode 74 due to MRI-induced energy on the inner conductor assembly 70, a plurality of samples of a bipolar lead 60 as described were tested. The inner first coil 82 and outer third coil 86 were wound in a left hand wind (LH), and the intermediate second coil 84 was wound in a right hand wind (RH) (relative to a proximal to distal view of the lead 60). Each sample was placed in a body simulating fluid and subjected to a 1.5 T simulated MRI environment. A temperature probe was connected to the electrode 74 to measure the temperature rise caused by signals induced in the inner conductive assembly 70. In each of the samples tested, the inner conductive assembly 70 included four filars and had a pitch of about 0.0203 in (0.0515 cm). The inner diameter of the inner conductive assembly 70 was 0.011 in (0.028 cm), and the outer diameter of the inner conductive assembly 70 was 0.048 in (0.122 cm). As is shown in the table below, samples were tested that included current suppression modules (CSM) 80 having proximal to distal lengths of 3.5 cm or 4.5 cm. The outer diameter of the outer conductive coil 66 in each of the samples tested was about 0.085-0.086 in (0.216-0.218 cm), and the diameter of the filar(s) of the outer conductive coil 66 was 0.004 in (0.010 cm).

TABLE 1

Electrode Heating

| Sample | CSM length (cm) | Outer coil winding direction | Number of outer coil filars | Outer coil pitch (in) | Temperature increase (° C.) | Temperature increase from unipolar (° C.) |
|---|---|---|---|---|---|---|
| 1 | 3.5 | LH | 1 | 0.0041 | 4.06 | 2.96 |
| 2 | 3.5 | RH | 1 | 0.0041 | 5.17 | 3.81 |
| 3 | 3.5 | LH | 2 | 0.0081 | 3.15 | 1.90 |
| 4 | 3.5 | RH | 2 | 0.0081 | 6.39 | 4.59 |
| 5 | 4.5 | LH | 1 | 0.0041 | 3.06 | 2.04 |
| 6 | 4.5 | RH | 1 | 0.0041 | 4.46 | 3.51 |
| 7 | 4.5 | LH | 2 | 0.0081 | 5.87 | 4.83 |
| 8 | 4.5 | RH | 2 | 0.0081 | 5.85 | 5.20 |

The "Temperature increase" column shows the overall temperature increase at the electrode 74 when the lead 60 is subjected to an MRI environment. The "Temperature increase from unipolar" column shows the difference in temperature increase at the electrode 74 when subjected to an MRI environment relative to a unipolar lead including only inner conductor assembly 70 (i.e., without the outer conductive coil 66). As is shown in Table 1, the configurations of the lead 60 having the outer conductive coil 66 wound in the same direction as the inner first coil 82 and outer third coil 86 (samples 1, 3, 5, and 7) generally exhibited a smaller temperature increase than configurations of the lead 60 having the outer coil 66 wound in the opposite direction as the inner first coil 82 and outer third coil 86 (samples 2, 4, 6, and 8). In addition, the unifilar leads lead having the longer current suppression module 66 (sample 5) exhibited the lowest overall temperature increase. Thus, it was demonstrated that, to minimize the interaction between the outer conductive coil 66 and inner conductor assembly 70 in an MRI environment, the outer conductive coil 66 is to be wound in the same direction as the coils 82 and 86.

In summary, embodiments of the present invention relate to an implantable medical device lead comprising an inner conductor assembly coupled to a first electrode at a distal end of the inner conductor assembly, and an outer conductive coil extending coaxially with the inner conductor assembly and coupled to a second electrode. The inner conductor assembly includes one or more filars arranged in a plurality of serially connected current suppression modules. Each current suppression module includes a first coil of the one or more filars wound in a first winding direction, a second coil of the one or more filars coaxial with the first winding and wound in a second winding direction opposite the first winding direction, and a third coil of the one or more filars coaxial with the first and second windings and wound in the first winding direction. The outer conductive coil includes one or more filars wound in the first winding direction.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

I claim:

1. An implantable medical device lead comprising:
a proximal connector;
an inner conductor assembly coupled to a first electrode at a distal end of the inner conductor assembly, the inner conductor assembly comprising one or more filars arranged in a plurality of serially connected current suppression modules, each current suppression module having a tri-layer configuration comprising an inner first coil of the one or more filars wound in a first winding direction, an intermediate second coil of the one or more filars coaxial with the first winding and wound in a second winding direction opposite the first winding direction, and an outer third coil of the one or more filars coaxial with the first and second windings and wound in the first winding direction; and
an outer conductive coil extending coaxially over the inner conductor assembly, the outer conductive coil having a proximal end coupled to the proximal connector and a distal end coupled to a second electrode and including one or more filars wound in the first winding direction from the proximal end to the distal end.

2. The implantable medical device lead of claim 1, wherein the outer conductive coil comprises two or fewer filars each having a filar diameter, and wherein a pitch of the outer conductive coil is less than three times the filar diameter.

3. The implantable medical device lead of claim 2, wherein the outer conductive coil comprises a single filar, and wherein the pitch of the outer conductive coil is less than two times the filar diameter.

4. The implantable medical device lead of claim 1, wherein each current suppression module has a length of between about 1.5 cm and 10 cm.

5. The implantable medical device lead of claim 1, wherein the inner conductor assembly comprises four filars.

6. The implantable medical device lead of claim 1, and further comprising:
an insulative layer between the inner conductor assembly and the outer conductive coil.

7. A medical device comprising:
a pulse generator; and
a lead including a lead body, a proximal connector, an outer conductive coil extending through the lead body, and an inner conductor assembly extending coaxially within the outer conductive coil,
the inner conductor assembly coupled to a first electrode at a distal end of the inner conductor assembly, the inner conductor assembly comprising one or more filars arranged in a plurality of serially connected current suppression modules, each current suppression module having a multi-layer configuration comprising a first inner coil of the one or more filars wound in a first winding direction, a second intermediate coil of the one or more filars coaxial with the first winding and wound in a second winding direction opposite the first winding direction, and a third outer coil of the one or more filars coaxial with the first and second windings and wound in the first winding direction,
the outer conductive coil having a proximal end coupled to the proximal connector and a distal end coupled to a second electrode and including one or more filars wound in the first winding direction from the proximal end to the distal end.

8. The medical device of claim 7, wherein the outer conductive coil comprises two or fewer filars each having a filar diameter, and wherein a pitch of the outer conductive coil is less than three times the filar diameter.

9. The medical device of claim 8, wherein the outer conductive coil comprises a single filar, and wherein the pitch of the outer conductive coil is less than two times the filar diameter.

10. The medical device of claim 7, wherein each current suppression module has a length of between about 1.5 cm and 10 cm.

11. The medical device of claim 7, wherein the inner conductor assembly comprises four filars.

12. The medical device of claim 7, and further comprising:
an insulative layer between the inner conductor assembly and the outer conductive coil.

* * * * *